United States Patent [19]

Boroschewski et al.

[11] 4,153,447

[45] May 8, 1979

[54] HERBICIDAL METHYLPHENYL CARBAMATES

[75] Inventors: Gerhard Boroschewski, Berlin; Friedrich Arndt, Aich, both of Fed. Rep. of Germany

[73] Assignee: Schering Aktiengesellschaft, Berlin, Fed. Rep. of Germany

[21] Appl. No.: 518,858

[22] Filed: Oct. 29, 1974

Related U.S. Application Data

[62] Division of Ser. No. 241,801, Apr. 6, 1972, Pat. No. 3,869,504.

[30] Foreign Application Priority Data

Apr. 27, 1971 [DE] Fed. Rep. of Germany ....... 2121957

[51] Int. Cl.$^2$ ............................................. A01N 9/20
[52] U.S. Cl. .................................................... 71/111
[58] Field of Search ........................................ 71/111

[56] References Cited

U.S. PATENT DOCUMENTS

| 3,404,975 | 10/1968 | Wilson et al. ........................ 71/101 |
| 3,535,101 | 10/1970 | Boroschewski et al. ................ 71/67 |

*Primary Examiner*—Catherine L. Mills
*Attorney, Agent, or Firm*—Michael J. Striker

[57] ABSTRACT

New herbicidal 4-Methylphenyl-bis-Carbamates, and their method of preparation are provided.

1 Claim, No Drawings

HERBICIDAL METHYLPHENYL CARBAMATES

This is a division of application Ser. No. 241,801, filed Apr. 6, 1972 now U.S. Pat. No. 3,869,504.

The present invention relates to new 4-methylphenyl-bis-carbamates, methods for their production and to herbicidal agents containing these compounds.

In the German Patent Disclosure No. 1,920,775 there is described the methyl-N-(3-(N'-(3',4'-dichlorophenyl)-carbamoyloxy)-4-methylphenyl) carbamate having herbicidal effect, which is said to be superior to the methyl-N-(3-(N'-(3'-methylphenyl)-carbamoyloxy)-phenyl)-carbamate already known to be in use.

It has now been found that compounds of the general formula

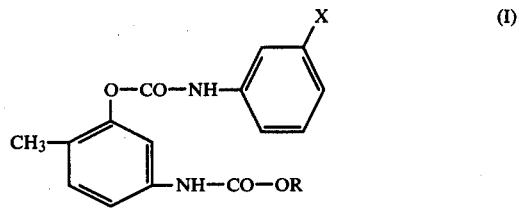

where R is an alkyl radical with 1 to 3 carbon atoms, X is a halogen, preferably chlorine, or alkyl, preferably methyl, which have a good herbicidal effect and are superior in this to the known 4-methylphenyl-biscarbamate.

The object of the invention therefore is to provide new compounds of the stated general formula (I), to methods for their production, and to herbicidal agents containing these compounds.

The compounds according to the invention possess, surprisingly, not only an increased herbicidal effectiveness as compared with the active substance of analogous constitution, but also have the advantage of good compatibility with cultivated plants. As cultivated plants, those to be named in particular are those which upon direct contact with the spray when treated in post emergence are as a rule particularly sensitive to herbicides, as for example beta beets and spinach.

Of the compounds according to the invention there are methyl-N-(3-(N'-(3'-methylphenyl)-carbamoyloxy)-4-methylphenyl)-carbamate and methyl-N-(3-(N'-(3'-chlorophenyl)-carbamoyloxy)-4-methylphenyl)-carbamate and which are effective because of their outstanding herbicidal properties. They prove particularly suitable for the control of field weeds, such as Stellaria media, Sinapis arvensis, Solanum, Senecio vulgaris, Lamium ssp., Amarantus retroflexus, Setaria ssp. and others.

The amounts to be used for sufficient weed control, particularly in the cultivations of beta beets and spinach, are approximately 0.3 to 3 kg of the active ingredient per hectare. This quantity can, surprisingly, be increased to 5 kg of active substance per hectare or more without damage to the crop cultivations, so that there is a considerable safety margin in the use of these compounds.

The compounds according to the invention can be used either alone or in mixture with other active substances. Optionally other plant protection or pest control agents, e.g. fungicides, nematocides or other agents, depending on the desired purpose, may be added. Also fertilizers may be added to the compounds as mixtures.

If a widening of the activity spectrum is intended, other herbicides may be added; although then the selectivity is naturally not always preserved. As mixture partners of herbicidal action, there are suitable added active substances from the groups of the carbamic and thiocarbamic acid esters, of the substituted anilines and anilides, triazines, amino-triazoles, diazines, such as uracils, e.g. 3-cyclohexyl-5,6-trimethylene uracil, 1-phenyl-4-amino-5-chloro-pyridazone(6), aliphatic carboxylic acids and halogen carboxylic acids, such as, 2,2-dichloropropionic acid or the salts thereof, tetrafluoropropionic acid or the salts thereof, esters of such carboxylic acids, ureas, 2,3,6-trichlorobenzyloxypropanol, rhodanium-containing agents and others.

Depending on the purpose of use, also other substances may be added, by which are to be understood also non-phytotoxic additions, which may give with herbicides a synergistic effect, such as wetting agents, emulsifiers, solvents, oily additions and others.

Appropriately the active substances according to the invention are employed in the form of preparations, such as powders, scatters, granulations, solutions, emulsions or suspensions, with addition of liquid and/or solid vehicles or diluents and possibly wetting, adhesive, emulsifying and/or dispersing aids.

Suitable liquid vehicles are, for example, water, aliphatic and aromatic hydrocarbons, such as benzene, toluene, xylene, cyclohexanone, isophorone, and mineral oil fractions.

As solid vehicles for use in the invention are suitable mineral earths, such as siliceous clay, silica gel, talc, kaolin, attaclay, limestone, silicic acid, and plant products, such as flours.

Among surface-active substances there may be used the following: calcium lignin sulfonate, polyoxyethylene-octylphenol ether, naphthalene sulfonic acids, phenol-sulfonic acids, formaldehyde condensates, fatty alcohol sulfate, and fatty acid alkali and alkaline earth salts.

The proportion of the active substance or substances in the various preparations may vary within wide limits. For example, the agents contain about 20 to 80 percent by weight of active substance, about 80 to 20 percent by weight of liquid or solid vehicles, and possibly up to 20 percent by weight of surface-active substances.

The application of the agents can be effected in the usual manner, such as with water as vehicle in spray solution quantities of 100 to 1000 liters/ha. For total weed control, necessary spray solution quantitites of more than 1000 liters/ha may be applied. Application of the agents in the so-called "ultra-low volume process" is possible, just as is their application in the form of so-called microgranulates.

The compounds of formula (I) not known until now are produced from the chloroformic acid-3-alkoxy-carbonylamino-6-methylphenyl ester by the reaction with chloranilines or toluidines or from 3-alkoxycarbonylamino-6-methylphenol and the respective isocyanates, preferably with addition of catalytic quantities of a tertiary organic base, such as triethylamine, or of an organic tin compound, such as dibutyl tin dilaurate. The compounds can be produced also from the corresponding 3-nitrophenyl-6-methyl-N-aryl carbamates by hydration of the nitro group to the amino group, for example, with the use of Raney nickel/hydrogen in methanol and subsequent reaction with chloroformic acid alkyl ester, preferably with addition of an inorganic or an organic tertiary base.

The production of compounds of the general formula (I) thus occurs by any of the following:
(a) by reaction of compounds of the general formula

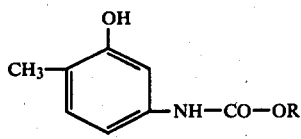  (II)

with isocyanates of the general formula

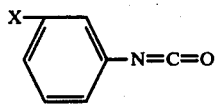  (III)

in the presence of a catalyst, preferably a tertiary organic base or an organic tin compound, or
(b) by reaction of compounds of the general formula

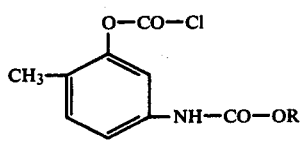  (IV)

with amines of the general formula

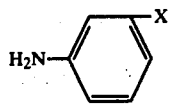  (V)

in the presence of an acid acceptor, or
(c) by the catalytic reduction of compounds of the general formula

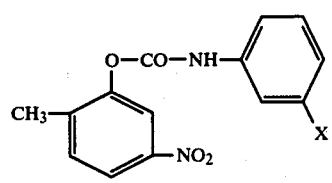  (VI)

to the corresponding amine and subsequent reaction with compounds of the general formula $$R - O - CO - Cl,$$  (VII)

where R and X have the above indicated meaning.

The following examples will explain and illustrate the production of the compounds according to the invention.

Methyl-N-(3-(N'-(3-chlorophenyl)-carbamoyloxy)-4-Methylphenyl) carbamate.

A solution of 9.06 g (0.05 mole) of 3-methoxycarbonylamino-6-methylphenol in 50 ml of tetrahydrofurane is admixed with 0.5 ml of triethylamine and 8.4 g of 3-chlorophenyl isocyanate. After 3 hours at room temperature, the reaction product is precipitated by addition of pentane.

Yield: 14.8 g = 88.5% of the theory.
M.p. 165°–166° C.

Methyl-N-(3-(N'-(3'-methylphenyl)-carbamoyloxy)-4-methylphenyl) carbamate can be produced analogously.
M.p. 175°–176° C.

The compounds according to the invention are insoluble in water and gasoline and soluble in acetone, tetrahydrofurane, dimethylformamide and dimethyl sulfoxide.

The herbicidal action of the compounds according to the invention will be evident from the following examples.

EXAMPLE

The plants listed below were treated in the greenhouse in post emergence with the compounds of the invention, methyl-N-(3-(N'-(3'-methylphenyl)-carbamoyloxy)-4-methylphenyl)-carbamate and methyl-N-(3-(N'-(3'-chlorophenyl)-carbamoyloxy)-4-methylphenyl) carbamate, as well as the reference agent methyl-N-(3-(N'-(3',4'-dichlorophenyl)-carbamoyloxy)-4-methylphenyl) carbamate, in amounts of 1 kg of active substance per hectare. The agents were applied as emulsions in 500 liters of water per hectare. The evaluation was made two weeks after the treatment.

| Agents according to invention | Amount used: 1 kg/ha | Crop plant Sugar beet | \multicolumn{7}{c}{Undesired plants} | | | | | | |
|---|---|---|---|---|---|---|---|---|---|
| | | | A | B | C | D | E | F | G |
| Methyl-N-(3-(N'-(3'-methylphenyl)carbamoyloxy)-4-methylphenyl) carbamate | 10 | 0 | — | 0 | 0 | — | — | 0 | |
| Methyl-N-(3-(N'-(3'-chlorophenyl)-carbamoyloxy)-4-methylphenyl) carbamate | 10 | 2 | 2 | 0 | 0 | 1 | 1 | 2 | |
| Reference agent | | | | | | | | | |
| Methyl-N-(3-(N'-(3',4'-dichlorophenyl)-carbamoyloxy-4-methylphenyl) carbamate | 10 | 9 | 6 | 6 | 3 | 6 | 5 | 6 | |

0 = totally destroyed
10 = without damage
Legend:
A = *Solanum sp.*
B = *Stellaria media*
C = *Senecio vulgaris*
D = *Lamium amplexicaule*
E = *Centaurea cyanis*
F = *Echinocloa crus galli*
G = *Setaria italica*

We claim:

1. The method for the selective control of weeds in fields containing crop plants and weeds which comprises post emergent application to such fields of the selective herbicide Methyl-N-(3-(N'(3'-chlorophenyl)-carbamoyloxy)4-methylhenyl)-carbamate in and amount sufficient to control the growth of weeds without substantial damage to the crop plants, said amount being from about 0.3 to about 3 kilograms per hectare.

* * * * *